United States Patent [19]

Paparizos et al.

[11] Patent Number: 4,727,207

[45] Date of Patent: Feb. 23, 1988

[54] PROCESS FOR CONVERTING METHANE AND/OR NATURAL GAS TO MORE READILY TRANSPORTABLE MATERIALS

[75] Inventors: Christos Paparizos, Willowick; Wilfrid G. Shaw, Lyndhurst, both of Ohio

[73] Assignee: Standard Oil Company, Cleveland, Ohio

[21] Appl. No.: 881,077

[22] Filed: Jul. 2, 1986

[51] Int. Cl.$^4$ ................................................ C07C 2/00
[52] U.S. Cl. ................................ 585/415; 585/500; 585/541; 585/648; 585/943; 585/650
[58] Field of Search ............... 585/500, 943, 415, 541, 585/648, 650

[56] References Cited

U.S. PATENT DOCUMENTS

| | | | |
|---|---|---|---|
| 1,677,363 | 6/1926 | Oliver | 585/943 |
| 1,917,627 | 7/1933 | Wulff | 585/943 |
| 1,988,873 | 1/1935 | Linckh et al. | 585/943 |
| 1,995,136 | 3/1935 | Winkler et al. | 585/500 |
| 2,037,056 | 4/1936 | Wulff | 260/170 |
| 2,061,598 | 11/1936 | Smith et al. | 585/500 |
| 2,151,167 | 3/1939 | Slatineanu | 585/500 |
| 2,180,672 | 11/1939 | Frey | 196/10 |
| 2,221,658 | 11/1940 | Waterman et al. | 585/943 |
| 2,326,553 | 8/1943 | Munday | 196/52 |
| 2,608,594 | 8/1952 | Robinson | 585/943 |
| 2,692,902 | 10/1954 | Pichler et al. | 585/943 |
| 2,823,243 | 2/1958 | Robinson | 585/500 |
| 3,234,300 | 2/1966 | Howard | 585/943 |
| 3,244,765 | 4/1966 | Fauser | 585/943 |
| 3,248,447 | 4/1966 | Lorenz et al. | 260/679 |
| 3,452,114 | 6/1969 | Friz et al. | 260/679 |
| 4,172,810 | 10/1979 | Mitchell et al. | 252/465 |
| 4,205,194 | 5/1980 | Mitchell et al. | 585/407 |
| 4,239,658 | 12/1980 | Mitchell et al. | 252/465 |
| 4,304,657 | 12/1981 | Miller | 208/135 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,450,310 | 5/1984 | Fox et al. | 585/400 |

FOREIGN PATENT DOCUMENTS 735978  6/1966  Canada ............................... 585/500

OTHER PUBLICATIONS

G. E. Keller and M. M. Bhasin, *Journal of Catalysis*, 73, 9–19, (1982).

Primary Examiner—William R. Dixon, Jr.
Assistant Examiner—Cynthia A. Prezlock
Attorney, Agent, or Firm—Larry W. Evans; David J. Untener; Raymond F. Keller

[57] ABSTRACT

The invention relates to a process for converting light hydrocarbon feedstocks such as methane and/or natural gas, to higher molecular weight hydrocarbon products that are more readily handleable and transportable. The process comprises heating a gaseous mixture comprising said light hydrocarbon feedstocks and carbon dioxide at a temperature of at least about 600° C. for a period of time effective to provide said higher molecular weight liquid hydrocarbon product. The invention also relates to the higher molecular weight liquid products obtained by the process of the invention.

20 Claims, No Drawings

PROCESS FOR CONVERTING METHANE AND/OR NATURAL GAS TO MORE READILY TRANSPORTABLE MATERIALS

TECHNICAL FIELD

This invention relates to a thermal process for converting methane and/or natural gas to liquid higher molecular weight products. This invention further relates to the use of carbon dioxide to assist such conversions where the yield of liquid products is enhanced.

BACKGROUND OF THE INVENTION

A major source of methane is natural gas which typically contains about 40-95% methane depending on the particular source. Other constituents include about 10% of ethane with the balance being made up of $CO_2$ and smaller amounts of propane, the butanes, the pentanes, nitrogen, etc.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commercial and industrial service.

Most processed natural gas is distributed through extensive pipeline distribution networks. As natural gas reserves in close proximity to gas usage decrease, new sources that are more distant require additional transportation. Many of these distant sources are not, however, amendable to transport by pipeline. For example, sources that are located in areas requiring economically unfeasible pipeline networks or in areas requiring transport across large bodies of water are not amendable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about $-162°$ C., transporting the gas, and revaporizing it are complex and energy intensive.

Still another approach has been the conversion of natural gas to higher molecular weight hydrocarbons that can be easily handled and transported, preferably substantially liquid hydrocarbons. The conversion of natural gas to higher order hydrocarbons, especially ethane and ethylene, would retain the material's versatility for use as precursor materials in chemical processing. Known dehydrogenation and polymerization processes are available for the further conversion of ethane and ethylene to liquid hydrocarbons. In these ways, easily transportable commodities may be derived directly from natural gas at the wellhead. A drawback in implementing such processes has been in obtaining a sufficient conversion rate of natural gas to higher molecular weight hydrocarbons.

The conversion of methane to higher molecular weight hydrocarbons at high temperatures, in excess of about 1200° C. is known. These processes are, however, energy intensive and have not been developed to the point where high yields are obtained even with the use of catalysts. Some catalysts that are useful in these processes (e.g., chlorine) are corrosive under such operating conditions.

Low temperature reactions (e.g., to 250° C. and 500° C.) of hydrocarbon feedstocks to higher molecular weight hydrocarbons is described in U.S. Pats. Nos. 4,433,192; 4,497,970; and 4,513,164. The processes described in these patents utilize heterogeneous systems and solid acid catalysts. In addition to the solid acid catalysts, the reaction mixtures described in the '970 and '164 patents include oxidizing agents. Among the oxidizing agents disclosed are air, $O_2$—$O_3$ mixtures, S, Se, $SO_3$, $N_2O$, NO, $NO_3$, F, etc.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9-19 (1982). This article discloses the use of single component oxide catalysts that exhibited methane conversion to higher order hydrocarbons at rates no greater than 4%. The process by which Keller and Bhasin oxidized methane was cyclic, varying the feed composition between methane and nitrogen and air (oxygen) to obtain higher selectivities.

The conversion of methane to higher molecular weight hydrocarbons using metal oxide catalysts and oxides of carbon which are generated from the hydrocarbon is described in U.S. Pat. No. 2,180,672. The conversion generally is carried out at temperatures of from about 150°-350° C., and the oxides of carbon are consumed in the reaction.

U.S. Pat. No. 1,677,363 describes the conversion of methane or natural gas to ethylenic hydrocarbons by heating a thin stream of methane or natural gas to a temperature not exceeding 950° C. U.S. Pat. No. 4,304,657 describes a process for converting feedstocks comprising aliphatic fractions boiling 70° C. Typically, the feedstock may be napthas, coker gasolines, FCC gasoline and pyrolysis gasolines. The process uses aromatization catalysts and a diluent which may be $CO_2$, CO or nitrogen, and the dilution is in a molar ratio of diluent to feed of from about 20:1 to 1:1. Preferred dilutions are 10:1 to 5:1 of diluent to fuel.

Methods for converting methane to higher molecular weight hydrocarbons at temperatures in the range of about 500° C. to about 1000° C. are disclosed in U.S. Pat. Nos. 4,443,644; 4,443,645; 4,443,646; 4,443,647; 4,443,648; and 4,443,649. The processes taught by these references provide relatively high selectivities to higher order hydrocarbons but at relatively low conversion rates, on the order of less than about 4% overall conversion. In addition to synthesizing hydrocarbons, the processes disclosed in these references also produce a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos. 4,172,810; 4,205,194; and 4,239,658 disclose the production of hydrocarbons including ethylene, benzene, ethane, propane and the like, in the presence of a catalyst-reagent composition which comprises: (1) a group VIII noble metal having an atomic number of 45 or greater, nickel, or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feed streams used in the processes disclosed in these patents do not contain oxygen. Oxygen is avoided for the purposes of avoiding the formation of coke in the catalyst. Oxygen is generated for the reaction from the catalyst; thus periodic regenerations of the catalysts are required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promoter metal selected from copper, rhenium, tungsten, zirconium, rhodium, and mixtures thereof.

It would be advantageous to provide a process for converting light hydrocarbons such as methane and/or natural gas to higher molecular weight liquid hydrocarbons that are more readily handleable and transportable.

SUMMARY OF THE INVENTION

A process is described for converting methane and/or natural gas to higher molecular weight liquid hydrocarbon products that are more readily handleable and transportable. The process comprises heating a gaseous mixture comprising said methane and/or natural gas and at least about 2% by volume of carbon dioxide at a temperature of at least about 600° C. for a period of time effective to provide said higher molecular weight hydrocarbon product. The invention also relates to the higher molecular weight liquid products obtained by the process of the invention.

DESCRIPTION OF THE PREFERRED EMBODIMENTS

The light hydrocarbon feedstocks that are converted to liquid hydrocarbons in accordance with the process of the invention are typically methane and/or natural gas. The methane which is treated in accordance with this invention may contain other materials such as ethane, ethylene, propane, etc. The natural gas that can be used can be either wellhead natural gas, as discussed above, or processed natural gas. The composition of processed natural gas varies with the needs of the ultimate user. A typical processed natural gas composition contains about 75–80% by volume methane, up to about 15% by volume of $CO_2$, about 5 to 10% by volume of ethane, the balance being made up of propane, butane and nitrogen. The conversion of natural gas containing small amounts of carbon dioxide, e.g., less than 2% by volume to liquid hydrocarbons can be improved in accordance with the present invention by adding more carbon dioxide to the natural gas before pyrolysis.

The conversion of the light hydrocarbon feedstocks to liquid hydrocarbon products is conducted in the presence of an effective amount of carbon dioxide. The carbon dioxide assists in the conversion of the methane and/or natural gas to higher molecular weight liquid hydrocarbons. The presence of the carbon dioxide results in higher conversion to liquid products, and the amount of tar or carbon formed in the pyrolysis reaction in relation to the amount of methane converted is reduced.

When the feedstock is methane, carbon dioxide must be added to form the desired gaseous mixture. When the feedstock is natural gas, it may not be necessary to add carbon dioxide if the natural gas contains at least 2% carbon dioxide.

The amount of carbon dioxide mixed with the methane feedstock can be varied from about 0.1 to about 50% by volume based on the volume of the feedstock. More often the amount of added carbon dioxide will be in the range of 0.1 to 25%, and most often in the range of 1–10% by volume.

When the feedstock is natural gas containing at least about 2% by volume of carbon dioxide, it may be unnecessary to add more carbon dioxide, but generally, the conversion to liquid product is increased by the addition of carbon dioxide to natural gas containing less than about 5% of carbon dioxide. The amount of carbon dioxide added to natural gas may be from 0.1 to about 50% by volume, and more generally from 0.1 to about 25% by volume.

The conversion of methane and/or natural gas feedstocks to higher molecular weight liquid hydrocarbon products can be conducted at temperatures above about 600° C., and the temperatures may be as high as 1300° C. Preferably, the pyrolysis reaction is conducted at temperatures above about 750° C., and even more preferably between about 800° C. to about 1200° C. For methane gas, a preferred temperature is about 1000° C. to about 1200° C.

The pyrolysis reaction can be conducted at subatmospheric, atmospheric or at elevated pressures up to about 50 atmospheres. Generally, the reaction is conducted at a pressure of from about 1 to about 10 atmospheres, and more generally at about 1 to 3 atmospheres.

The period of time for heating the gaseous mixture of methane and/or natural gas and the carbon dioxide (or residence time in the reactor) is generally a time which is sufficient to provide the desired conversion to higher molecular weight liquid hydrocarbon products. However, the reaction time or residence time should not be so long as to provide sufficient time for the products obtained to decompose. Accordingly, contact or residence time in the range of from about 0.1 to about 5000 milliseconds have been found to be useful with contact times in the range of from about 1 to about 1500 milliseconds generally being sufficient. Contact times of from about 20 to about 1000 milliseconds are most preferred.

The overall composition of the higher molecular weight hydrocarbon products produced in accordance with the process of the invention may vary somewhat depending upon the nature (source) of the methane and/or natural gas that are initially used as feedstock, and the condition under which they are processed. For example, the higher molecular weight hydrocarbon product will typically consist of hydrocarbons containing two or more carbon atoms. These hydrocarbon products generally consist of mixtures of both aliphatic and aromatic materials. Since the process of the present invention is well-suited to a continuous, cyclic process, the lighter weight gaseous hydrocarbon products such as ethane or propane, etc. can be separated from the more desirable higher molecular weight liquid hydrocarbon products and recycled in the process for further conversion to higher molecular weight liquid hydrocarbon products. Unsaturated hydrocarbons such as ethylene acetylene, propylene, etc., may be present in the gaseous hydrocarbon products obtained in this invention and these may be recycled through the process for conversion to higher molecular weight liquid products.

The preferred higher molecular weight hydrocarbon products made by the process of the present invention are aliphatic and/or aromatic products that are sufficiently liquid to be readily handleable and transportable in conventional pipeline systems. Included in this preferred group are hydrocarbons containing at least about 5 carbon atoms, more particularly, aromatic compounds containing at least 6 carbon atoms. The references in this application to "liquid hydrocarbons" is intended to include hydrocarbons that are substantially in the liquid form at a temperature of about 25° C. and a pressure of one atmosphere.

The apparatus that can be used in the process of the present invention can be any conventional pyrolysis reactor system that is adapted to the specific gaseous reactants and high molecular weight products provided for in the process of the invention. Such pyrolysis reactors include fired tubular heaters, pebble-bed heaters and regenerative furnaces, but fired tubular heaters are the generally preferred type of reactor. These reactors can be made from a variety of materials which can withstand high temperatures. A more detailed description of such apparatus can be found in the Encyclopedia of Chemical Technology, Kirk and Othmer, Ed. Third Edition, Vol. 9, pp. 400-11 which is incorporated herein by reference. The design and construction of such apparatus is within the skill of the art and thus need not be described further herein.

In one preferred embodiment, the process of the invention is carried out in the absence of any solid catalyst, particularly solid aromatization catalysts. Such catalysts are not required in the present pyrolysis reaction.

In order to further illustrate the present invention, the following examples are provided. Unless otherwise indicated in the following examples and elsewhere in the specification and claims, all parts and percentages of products are by weight and those of the feed are by volume; all temperatures are in degrees centigrade.

In each of the following examples, the feedstock indicated in the table is introduced into a quartz tube reactor that is surrounded by an electric furnace to provide the desired temperature. The control samples contain no added carbon dioxide initiator. In operation, the gaseous feed composition is advanced through the quartz tube and the exiting product is collected in containers cooled with dry ice and acetone. The "liquids" identified in the following table are those materials which condense in the cooled containers. The weight percentage of the liquid products is calculated by weighing the liquids formed and dividing that weight by the amount of methane or natural gas in the feed composition and multiplying by 100. The selectivity is defined by dividing the weight of product formed by the weight of consumed hydrocarbon feed and multiplying by 100. The conversion is defined by dividing the hydrocarbon that is converted by the hydrocarbon consumed and multiplying by 100. The gases that are obtained from the process are analyzed using a Carl 400GC chromatograph.

EXAMPLES C-1 and 1-3

In these examples, methane is used as the feedstock. The pyrolysis temperature is 1110° C., the diameter of the quartz reactor is 5 mm., and the contact time is about 600 milliseconds. Example C-1 is a control in which no $CO_2$ is added. In Examples 1-3 respectively, 5, 10, and 15% by volume of $CO_2$ are added. Other particulars of these examples, including the results are summarized in Table I. The results demonstrate the improved results when $CO_2$ is added including increased formation of liquids and higher selectivity to liquids and $C_2$ hydrocarbons.

TABLE I

| Example | C-1 | 1 | 2 | 3 |
|---|---|---|---|---|
| Feed: | | | | |
| $CH_4$ (% v) | 100 | 95 | 90 | 85 |
| $CO_2$ (% v) | — | 5 | 10 | 15 |
| Methane conv. (%) | 20.7 | 20.2 | 18.4 | 19.4 |
| Liquids formed (%) | 7.3 | 10.7 | 12.0 | 12.6 |
| Selectivity to liquids (%) | 35.5 | 53.4 | 65.5 | 65.5 |
| Selectivity to $C_2$ plus hydrocarbons (%) | 58.3 | 78.4 | 93.9 | 90.9 |

EXAMPLES C-2 and 4-7

In these examples, the feedstock is a mixture of methane, 51% by volume ethane and 2% by volume of propane; the pyrolysis temperature is 1125° C.; the diameter of the quartz reactor is 3 mm.; and the contact time is about 70 milliseconds. Example C-2 is a control example in which no $CO_2$ is added. In Examples 4-7 respectively, 5, 10, 15 and 18.5% by volume of $CO_2$ are added. The improved selectivities obtained in the examples where $CO_2$ is added is evident from the results summarized in Table II.

TABLE II

| Example | C-2 | 4 | 5 | 6 | 7 |
|---|---|---|---|---|---|
| Feed: | | | | | |
| $CH_4$ (% v) | 93 | 88 | 83 | 77 | 74.5 |
| $C_2H_6$ (% v) | 5 | 5 | 5 | 5 | 5 |
| $C_3H_8$ (% v) | 2 | 2 | 2 | 2 | 2 |
| $CO_2$ (% v) | — | 5 | 10 | 15 | 18.5 |
| Liquids formed (%) | 7.7 | 7.6 | 9.3 | 8.8 | 9.8 |
| Selectivity to liquids (%) | 30.3 | 34.4 | 39.4 | 39.2 | 46.2 |
| Selectivity to $C_2$ plus hydrocarbons (%) | 62.9 | 76.3 | 77.4 | 88.4 | 96.7 |

As can be seen from the results summarized in the above tables, the presence of carbon dioxide in accordance with the process of this invention results in an increased yield of liquids and an increase in the selectivity to useful products.

While the invention has been explained in relation to its preferred embodiments, it is to be understood that the various modifications thereof will become apparent to those skilled in the art upon reading this specification. Therefore, it is to be understood that the invention disclosed herein is intended to cover such modifications as fall within the scope of the appended claims.

We claim:

1. A thermal process for converting a feedstock comprising methane and/or natural gas to liquid hydrocarbons comprising heating a gaseous mixture comprising said feedstocks and at least about 2% by volume of carbon dioxide to a temperature of at least about 1000° C. for a period of time effective to provide said liquid hydrocarbons.

2. The process of claim 1 wherein the feedstock comprises methane, and carbon dioxide is added to form the gaseous mixture.

3. The process of claim 1 wherein the feedstock comprises natural gas containing at least about 2% by volume of carbon dioxide.

4. The process of claim 3 wherein from about 0.1 to about 25% by volume of carbon dioxide is added to the natural gas.

5. The process of claim 1 wherein the mixture is heated to a temperature of from about 1000° C. to about 1200° C.

6. The process of claim 1 wherein the gaseous mixture is heated for a period of from about 0.1 to about 5000 milliseconds.

7. The process of claim 1 wherein the feedstock comprises methane and the gaseous mixture is heated to a temperature of from about 1000° C. to about 1200° C.

8. A thermal process for converting a feedstock consisting essentially of methane to liquid hydrocarbons comprising heating a gaseous mixture of said feedstocks and at least about 2.0% of carbon dioxide to a temperature of at least about 1000° C. for a period of time effective to provide said liquid hydrocarbons.

9. The process of claim 8 wherein the gaseous mixture comprises from about 2 to about 50% by volume of the added carbon dioxide based on the volume of the feedstock.

10. The process of claim 8 wherein the gaseous mixture from about 2 to about 25% by volume of the added carbon dioxide based on the volume of feedstock.

11. The process of claim 8 wherein the gaseous mixture contains from about 2 to about 10% by volume of the added carbon dioxide based on the volume of the feedstock.

12. The process of claim 8 wherein the gaseous mixture is heated for a period of from about 0.1 to about 5,000 milliseconds.

13. The process of claim 8 wherein the gaseous mixture is heated for a period of from about 20 to about 1000 milliseconds.

14. The process of claim 8 wherein the gaseous mixture is heated to a temperature within the range of from about 1000° C. to about 1300° C.

15. The process of claim 8 wherein the gaseous mixture is heated to a temperature of from about 1000° C. to about 1200° C.

16. A process for converting methane and/or natural gas feedstocks to higher molecular weight liquid hydrocarbon products which comprises heating a gaseous mixture comprising said feedstocks and from about 2 to about 10% by volume, based on the volume of said feedstock, of carbon dioxide to a temperature of from about 1000° C. to about 1300° C. for a period of time of from about 20 to about 1000 milliseconds.

17. The process of claim 16 wherein the feedstock is natural gas.

18. The process of claim 16 wherein the feedstock is methane.

19. The process of claim 16 wherein the feedstock comprises methane, and the gaseous mixture is heated to a temperature of from about 1000° C. to about 1200° C.

20. The process of claim 16 wherein the liquid hydrocarbon product is recovered from the gases, and the gases are recycled through the process.

* * * * *